(12) United States Patent
Colin et al.

(10) Patent No.: US 6,902,706 B1
(45) Date of Patent: Jun. 7, 2005

(54) VALVES ENABLING A LIQUID TO BE DIRECTED IN A DIAGNOSTIC CHART DIAGNOSTIC CHARTS AND DIAGNOSTIC DEVICE COMPRISING SEVERAL CHARTS

(75) Inventors: Bruno Colin, Marcy l'Etoile (FR); Jacques Dachaud, Besancon (FR)

(73) Assignee: Biomerieux S.A., Marcy l'Etoile (FR)

( * ) Notice: Subject to any disclaimer, the term of this patent is extended or adjusted under 35 U.S.C. 154(b) by 405 days.

(21) Appl. No.: 10/009,824

(22) PCT Filed: Jun. 21, 2000

(86) PCT No.: PCT/FR00/01719

§ 371 (c)(1),
(2), (4) Date: Dec. 13, 2001

(87) PCT Pub. No.: WO00/78453

PCT Pub. Date: Dec. 28, 2000

(30) Foreign Application Priority Data

Jun. 22, 1999 (FR) ............................ 99 08116

(51) Int. Cl.[7] ................................ B01L 11/00
(52) U.S. Cl. ................ 422/103; 422/115; 422/100; 422/99
(58) Field of Search ................ 422/100, 103, 422/113; 251/12

(56) References Cited

U.S. PATENT DOCUMENTS 3,998,571 A * 12/1976 Falke ....................... 417/569
4,852,851 A * 8/1989 Webster ..................... 251/61.1
5,735,501 A * 4/1998 Maurer et al. ............. 251/85
5,945,334 A * 8/1999 Besemer et al. ........... 435/287.2
6,406,605 B1 * 6/2002 Moles ........................ 204/601

FOREIGN PATENT DOCUMENTS

| EP | 0 779 103 | * | 6/1997 |
| GB | 2 097 692 | * | 11/1982 |
| WO | WO 97/22825 | * | 6/1997 |
| WO | WO 97/27324 | * | 7/1997 |
| WO | WO 98/00231 | * | 1/1998 |
| WO | WO 99/03584 | * | 1/1999 |

* cited by examiner

*Primary Examiner*—Jill Warden
*Assistant Examiner*—Jyoti Nagpaul
(74) *Attorney, Agent, or Firm*—James C. Lydon

(57) ABSTRACT

A valve (2), crossed by at least one channel (3), allowing to direct at least one fluid (F5) displaced by a transfer device within a test sample card (1), the card (1) featuring two faces (4 and 5) connected to one another (4) (5) by an edge (6). A card equipped with a device allowing several cards equipped with such valves to be implemented is made up of a flexible film (7), and/or which can be distorted, part of which is fixed to at least one of the faces (4 and/or 5) of said card (1) on the one hand, and a film compression device (7), which can be deactivated on the other hand. In addition, securing is carried out on at least one of the plane faces (4 and/or 5), for example, by a securing device located at the level of a recession (9) peripheral to the valve (2), such as a groove (9). The valve is particularly applicable in the field of diagnosis.

23 Claims, 4 Drawing Sheets

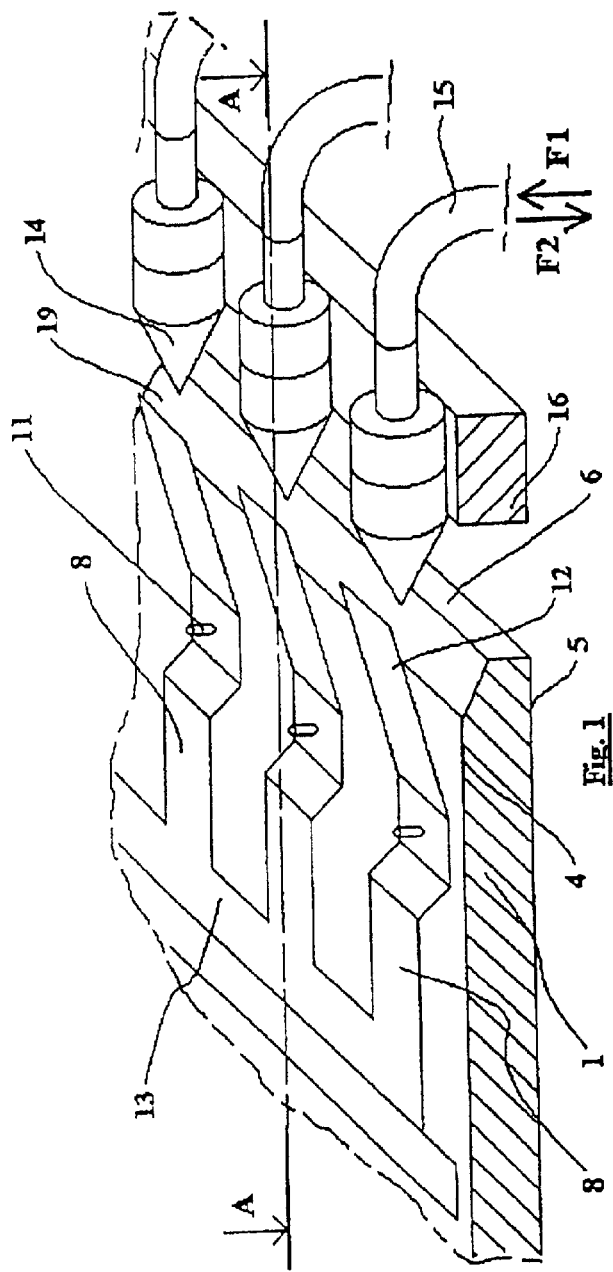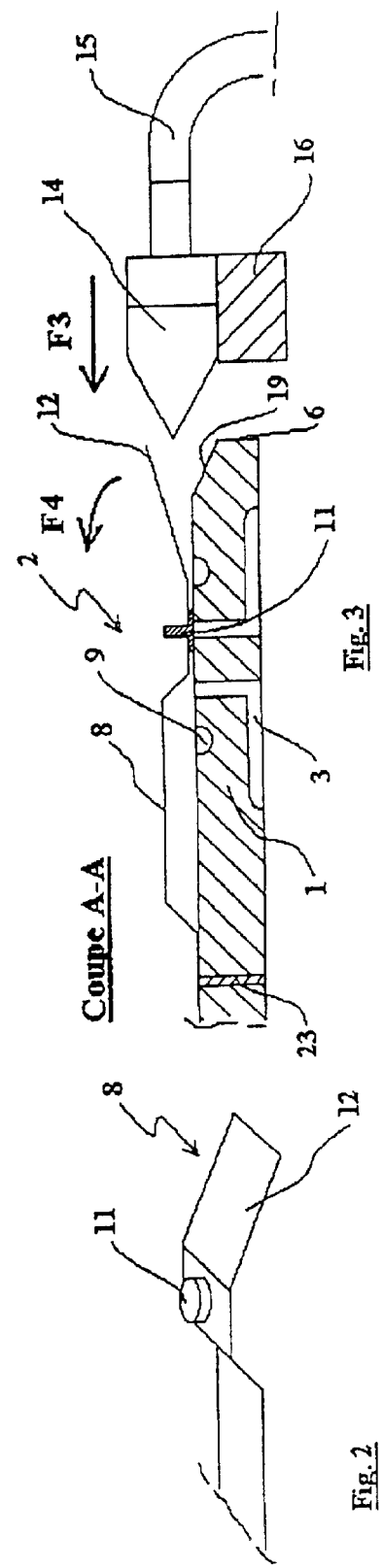

Coupe B-B

Coupe C-C

VALVES ENABLING A LIQUID TO BE DIRECTED IN A DIAGNOSTIC CHART DIAGNOSTIC CHARTS AND DIAGNOSTIC DEVICE COMPRISING SEVERAL CHARTS

This application is a U.S. National Stage of International application PCT/FR00/01719, filed Jun. 21, 2000 and published on Dec. 28, 2000 in the French Language, and which claims priority of French Patent Application 99/08116, filed Jun. 22, 1999.

DESCRIPTION

This invention concerns the field of valves used to direct at least one fluid displaced by transfer systems within a test sample card. It also concerns a card equipped with a device allowing several cards equipped with such valves to be implemented.

Up until now, most test sample cards have recesses on both of their plane and parallel faces as well as crosswise recesses, all of the recesses forming a channel network in which one or more fluids are displaced. On the face of the cards, said recesses are marked out by adhesive films. Fluid displacement is controlled by valves.

This type of structure is not reusable, as a valve can only be used efficiently once. Thus, when the valve is tipped into closed position, the adhesive surface of the film also comes into contact with the rest of the card, and the valve can therefore no longer be used. The valve remains in closed position.

The only solution thus remaining is the deposit on an inert, that is non-adhesive film, of an adhesive layer having cut-outs which have been previously removed by a punch.

Technically speaking, this is not easy to achieve. Also, the cost of manufacturing such film in addition to the difficulties encountered in positioning the film on the test sample card would be incompatible with mass production in large quantities.

The applicant filed a patent application on Sep. 8, 1998, under application number FR98/11383. This invention concerns a device or test sample card enabling a reaction or at least two reactions to be conducted therein in parallel or in series. The device consists of a network of channels wherein the transfer of at least one sample to be treated and/or analyzed is possible, on the one hand, and at least one valve built into the device, on the other hand, enabling the orientation of each sample transferred at the network level and thus the control of transfers, reactions and analyses in said device. In the embodiment shown in FIGS. 1 through 3, it can be seen that an elastomer disk is inserted between the adhesive film ard the body of the card, which allows the valve to be reused.

This structure thus provides a solution, although it increases the number of elements and the manufacturing cost of a functional test sample card.

Document WO-A-97/27324 attempts to provide a solution to this problem. Thus, it concerns a cassette to conduct reactions in parallel which features an entry and exit orifice to transfer the sample(s) to be introduced into the cassette. Valves are present at cassette level, which have a particular construction (Bursapak chamber, piston valve, bead valve). Under a continuous outside force, these valves allow a channel to be held closed. In this embodiment, the film is heat-sealed to the cassette.

However, this construction has a major disadvantage. The disadvantage resides in the deformation of the face of the cassette onto which the film is heat-sealed. While this face is originally plane, the heat-sealing weld causes distortion which is detrimental to subsequent proper use of the cassette. This could range from an error in manipulation and/or analysis to rendering the valves inoperable. The worst problems may be encountered when this type of cassette is used by an automated controller, which is generally the case. In this configuration, the card, which is warped by the heat-seal, may block or even damage the automated controller assembly.

Another disadvantage of this innovation is that it is absolutely necessary that the film is precisely heat-sealed onto the card. Even a tiny error may lead to channel blockage and/or valve leakage.

This invention provides a concrete response to all of the disadvantages of prior art. Thus, the film is heat-sealed onto the body of the test sample card without damaging the surface where the heat-seal is made. Furthermore, the tolerance for the heat-sealing position is greater, as it only outlines the area that makes up the valve and does not follow it closely.

To this effect, this invention concerns a valve, with at least one channel running through it, allowing at least one fluid displaced by transfer means within the test sample card to be directed, the card featuring two faces connected one another by an edge, characterized in that it consists of a film, which is flexible and/or which can be deformed, secured partly on at least one of the faces of said card, and by a film compression means, which can be activated or deactivated, and in that their securing is made at least on one of the faces, for example a plane one, by a securing means located at the level of a recession surrounding the valve, such as a groove.

According to an alternative embodiment, the securing of the film on the card is peripheral to the set of channels concerned by the valve (i.e. at least one fluid entry channel and at least one fluid exit channel), both fluids may be identical or different.

According to another alternative embodiment, the securing is carried out by a heat seal peripheral to the valve.

According to still another alternative embodiment, the compression means acts on the film at the intersection between at least one of the valve channels and the face of the card in question.

According to yet another alternative embodiment, the compression means consists of a flexible tab.

According to yet another alternative embodiment, the compression means features a closure mechanism, such as an elastomer pin, and an opening or closing mechanism, such as a wedge, which synergizes with actuation mechanisms.

According to a preferred embodiment, at least two valves are positioned side by side, and the means assigned to compressing the valves, the latter being positioned side by side, are connected together to form a strip assembly.

Preferably, two adjacent valves positioned side by side are separated by spacing of between 1 and 5 mm, and preferably with spacing having values used in the field of electronics, such as 3.96 mm, 2.54 mm or 1.28 mm.

According to another preferential embodiment, the film near the valve is in contact with the plane face of the card when said valve is in closed position, and is elevated in relation to said plane face when the valve is in open position.

The invention also concerns a test sample card made up of a multiplicity of valves described above which are, fully or partly, distributed along at least one edge of said card.

When the card is in more or less parallelepiped arrangement, the edge(s), where the valves are located, is (are) rectilinear, and the distance separating said edge is constant, in relation to the location of each valve.

The invention concerns a device enabling the implementation of several cards, described above. This device consists of the following:
- a storage area for the cards which are placed parallel to one another,
- a valve opening and closing inspection area associated with manual or automatic control, and
- an intermediate area used as an interface between the storage and inspection areas.

According to a preferential embodiment, the cards are arranged in the storage area with all valves on the same edge located within the same plane facing the intermediate area; the inspection area consists of actuators, such as electromagnets, whose longitudinal movements are made in the direction of said intermediate area, and this intermediate area consists of maneuvering pins having at least two positions, one position which allows valve opening and the other allowing valve closure.

According to another embodiment, the device features one actuator per card and one maneuvering pin per valve.

According to yet another embodiment, the actuator's movement is coaxial to the longitudinal axis of the maneuvering pin and valve, which is activated and deactivated.

According to yet another embodiment, all of the actuators are installed in the same plane and are mobile along an axis parallel to the plane formed by all of the edges of the cards having valves which could be actuated by these actuators.

According to another embodiment, the maneuvering pins have two possible positions, one allowing the valves to be opened and the other allowing the valves to be closed, each position being on each side of a confining element.

Preferably, the confining element is mobile between two extreme positions, one where it prevents any pin movement and the other where the movement of said pins is possible.

The accompanying drawings are given by way of example and are not to be taken as in any way limiting. They are intended to make the invention easier to understand.

FIG. 1 represents a perspective view of a test sample card according to a preferred embodiment of this invention.

FIG. 2 represents a perspective view of the bottom of one of the flexible strip assemblies shown in FIG. 1.

FIG. 3 shows a cross-sectional view through A—A in FIG. 1.

Figure 12:
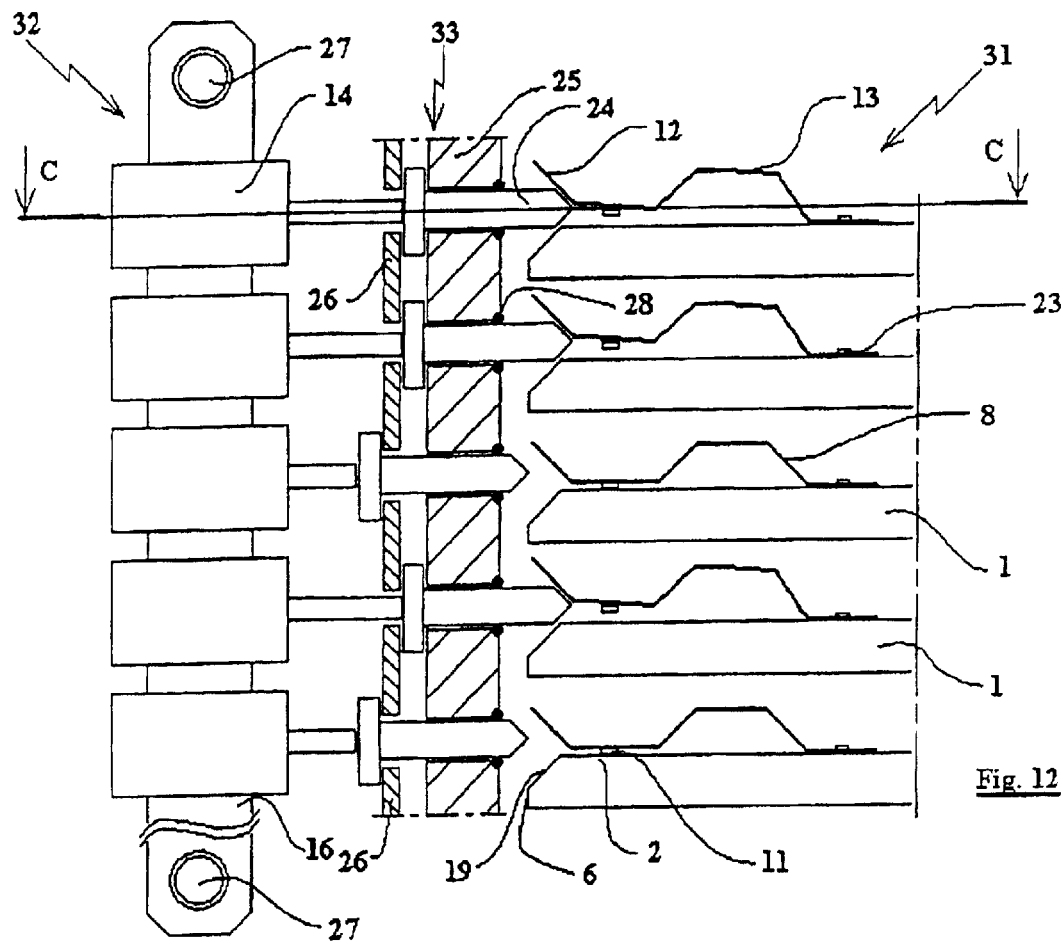
FIG. 12 represents a partial cross-sectional view of a device allowing several cards equipped with the valves described above to be implemented.
Figure 13:
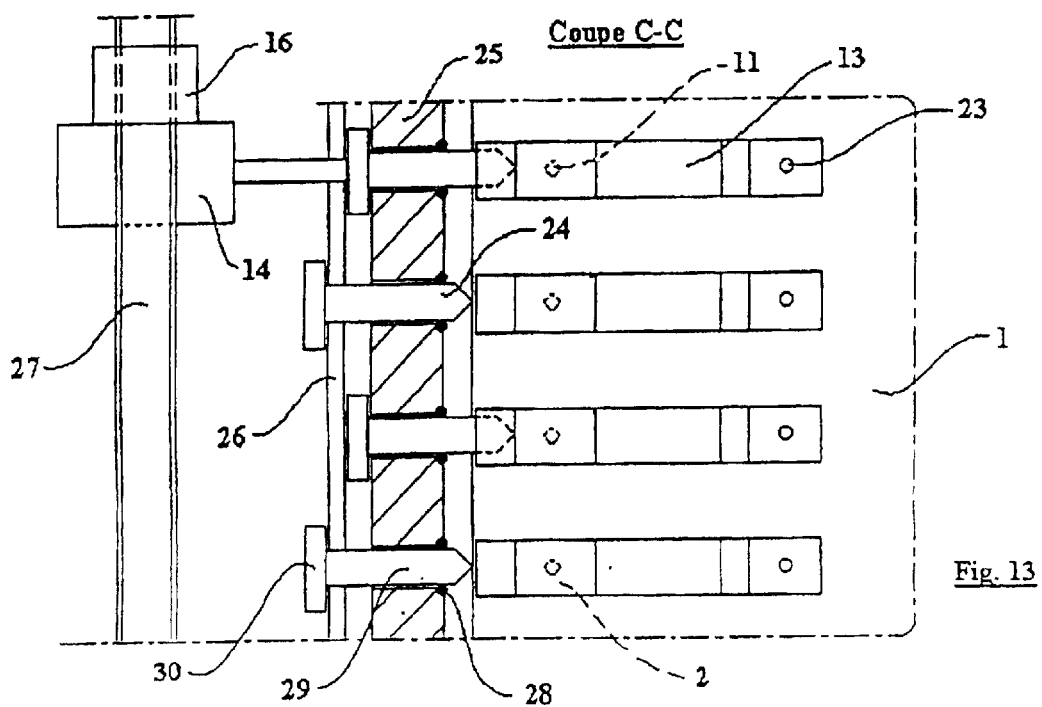

Finally, FIG. 13 shows a cross-sectional view through C—C in FIG. 12.

Figure 8:
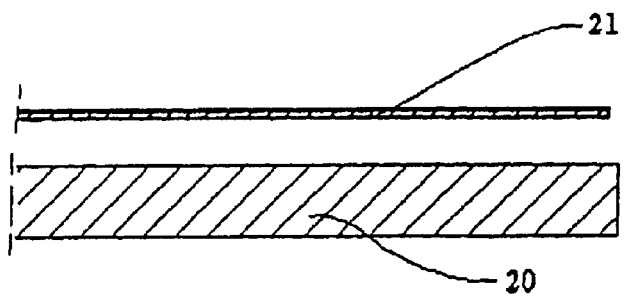
FIG. 8 represents a cross-sectional view, prior to assembly by heat-sealing, of a test sample card body and a flexible film according to background art.
Figure 9:
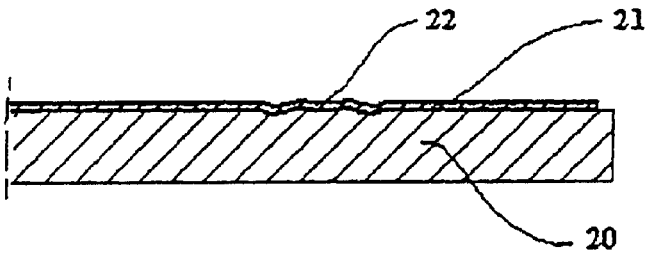
FIG. 9 represents a cross-sectional view, after assembly by heat-sealing, of a test sample card body and a flexible film according to background art.

This invention concerns the problems of heat-sealing films onto a solid support such as the body of the test sample card. The background art is well represented in FIGS. 8 and 9 where it can be seen that the card 20 consists essentially of two opposite faces, parallel to one another and perfectly flat. A film 21 is located in the vicinity of one of these faces, as is clearly shown in FIG. 8. After heat-sealing 22 has been performed, it can be clearly seen on FIG. 9 that the body 20 is distorted and also lead the film 21 to be distorted. In this manner, this distortion induces depressions and elevations on the surface of the body of the card 20 which are detrimental to further use of this card, and which can also cause weakening in certain spots of the film 21. The assembly may be damaged and possibly prevent the card from being used for future analyses.

The purpose of this invention is thus to eliminate the problem of heat-sealing films onto a support, such as a test sample card which is generally made of plastic material.

Figure 10:
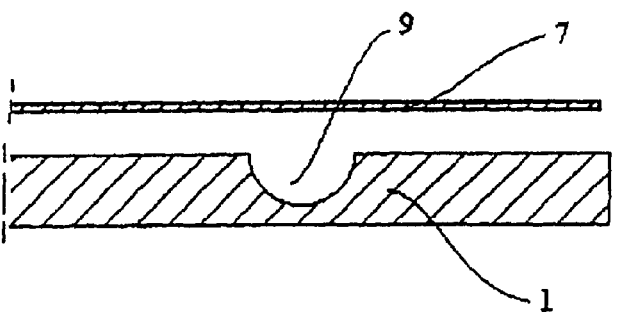
FIG. 10 represents a cross-sectional view, prior to assembly by heat-sealing, of a test sample card body and a flexible film according to this invention.
Figure 11:
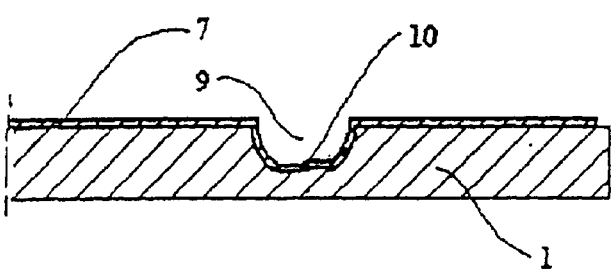
FIG. 11 represents a cross-sectional view, after assembly by heat-sealing, of a test sample card body and a flexible film according to this invention.

In FIGS. 10 and 11, it can be seen that the body of said card 1 features a groove 9 or recession in a certain location which will receive therein part of the flexible film 7, said film 7 and the body of the card 1 being held together by a weld 10 located in the bottom of the groove 9. As a result, the heat-seal weld 10 does not distort the upper surface of the card 1 and thus presents no subsequent problem in using said card 1 and in performing analyses.

FIG. 1 shows a general perspective view of an embodiment according to the invention. The valves are partially represented as will be discussed below. Thus in this figure, the flexible film 7 as well as all of the elements that make up the valve inside the body of the card 1 are not represented although they are actually present. Nevertheless, the elements which are represented are important. Firstly, a strip assembly 13 can be seen which is made up of several tabs 8 and is fixed on the card 1 by a securing means 23. These tabs 8 extend onto one fo the sides of the strip assembly 13 more or less perpendicularly to this strip assembly 13, with all of the tabs 8 being parallel to each other. In addition, the distance separating two adjacent tabs 8 is constant, in such a way that there is a space separating all of the adjacent tabs 8. Preferably, this distance is identical to the spacing used in electronic applications, in order to reduce the cost of manufacturing strip assemblies 13 or to use actuators which already exist in the background art. Such spacing may be between 1 and 5 mm, and more precisely is equal to 3.96 mm, 2.54 mm or 1.28 mm.

At the level of said blade strip assembly 13, there is direct contact between the body of the card 1, and of course between the film 7, not shown in this figure, and this strip assembly 13. Toward the right-hand side of the figure, an oblique face can be seen then a face parallel to the upper surface of the card 1 and finally another oblique face, both oblique faces forming an angle of more or less 90° between them, although this value is in no way limiting. At the bottom of the second oblique face, there is another parallel face near the upper surface of the card 1. This face enables the channel 3, that is integral with the underlying valve 2, to be directly opened or closed. On the right-hand side of this face there is a last beveled face 12 designed to synergize with a piston-type actuator 14, located at the far right of this figure.

The head of the piston-type actuator 14 is cone shaped; this shape allows the head to engage between the beveled edge 12 of the opening means of the flexible tab 8 and the beveled surface 19 of the card 1. This beveled surface 19 is present between the first upper face 4 and the edge 6 of said card 1, with this card 1 also including a second lower face 5.

The face of the flexible tab 8, which allows closure, is equipped with a closing means 11 or an elastomer pin 11 whose function will be described later. This pin 11 and the opening means or beveled face 12 are clearly shown in FIG. 2.

In both FIGS. 1 and 3, it can be seen that the whole set of piston-type actuators 14 is mounted on a support 16, while each piston-type actuator 14 is supplied with compressed air in the direction of F1 or F2 by means of compressed air hoses 15.

In FIG. 3 and in combination with FIG. 1, it is easier to understand how this device works. When compressed air enters the hose 15, the piston-type actuator 14 is displaced in the direction of F3 and the tab 8 is pushed in the direction of F4. When, conversely, the compressed air leaves the system in the direction of F2, the movements of the piston-type actuator 14 and the tab 8 are reversed in relation to arrows F3 and F4 in FIG. 3.

In FIG. 3 it can be seen that valve 2 is closed when the closing means or elastomer pin 11 compresses the intersection point of a channel 3 with the surface of the test sample card 1 where the film 7 is located.

Figure 4:
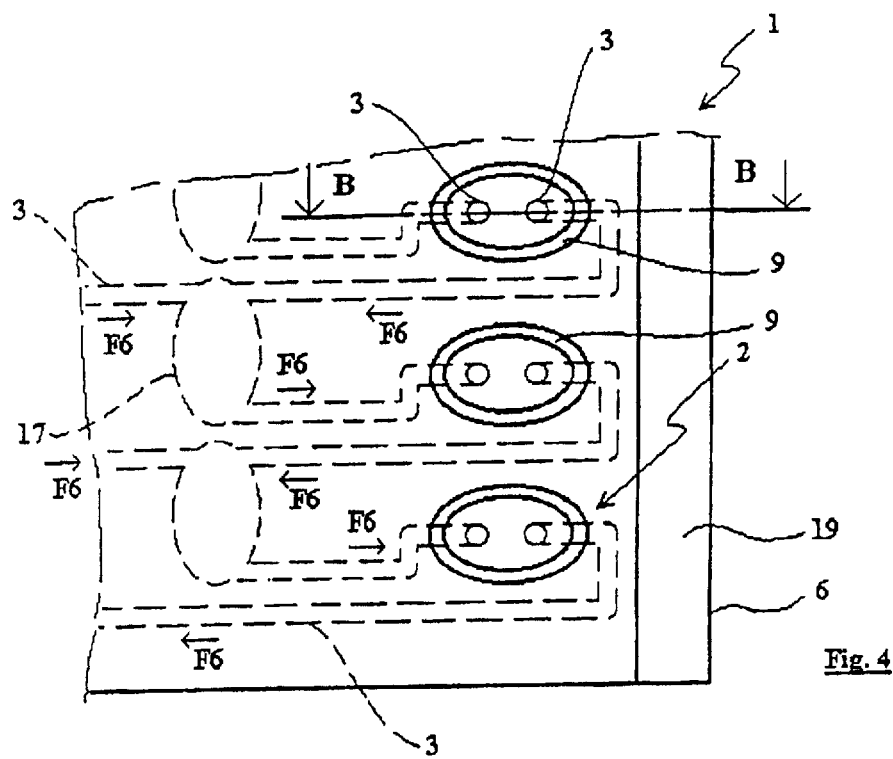
FIG. 4 represents a view of the top of the test sample card, with the tabs removed.
Figure 5:
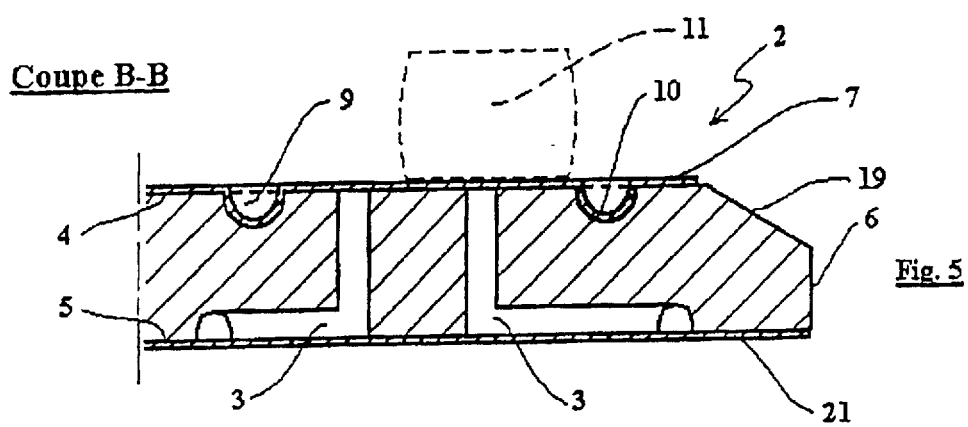
FIG. 5 represents a cross-sectional view along B—B of FIG. 4, when the valve is in closed position.

FIG. 4 represents a top view of FIG. 1 in the case where all of the flexible tabs 8 have been removed. In this case, it can be seen that each valve 2 is made up of a small plane surface on the same level as the rest of the plane surface of said card 1 (also see FIGS. 5 and 6), this small surface including at least one inlet channel 3 and one outlet channel 3, the intersection point between this surface and the fluid input and output channels 3 being in contact with the film 7 as can be clearly seen in FIG. 5. In this case, the valve is closed. In FIG. 5, it can be seen that the elastomer pin 11 is schematically represented in order to clearly show that it blocks one of the two channels 3. Of course, the pin 11 may block either channel or both channels 3. Furthermore, the valve may have more channels, that is three or more.

It can also be seen that the card features a certain number of compartments 17. The compartments 17 are connected to the valves by means of channels 3. It is also possible, although not represented in the figure, that other valves and other compartments are located on the rest of the card 1 which allows mixing between two networks of channels 3 located in parallel and not in series. This is clearly represented in FIG. 4 where it can be seen that the movement of fluids in the direction of F6 on the card 1 may bring two liquids together for mixing or for analysis within a compartment 17.

Figure 6:
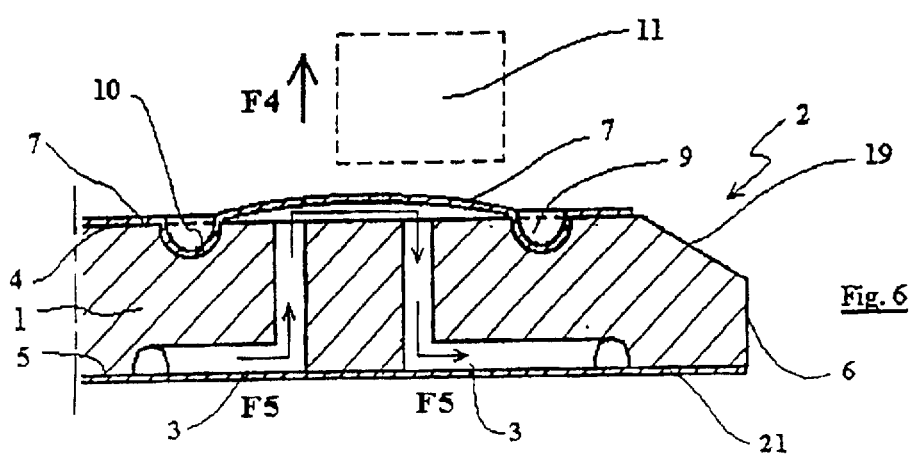
FIG. 6 represents a cross-sectional view identical to FIG. 5, when the valve is in open position.

In FIGS. 5 and 6, it can now be seen that, on the upper valve 4 of card 1, there is a flexible film 7 which is not adhesive, as explained in the section dealing with background art. This film 7 is thus heat-sealed in the peripheral groove 9 around the valve 2. Nevertheless, on the bottom face 5 of said card 1, an adhesive film 21, well know in prior art, can also be used. Of course, depending on the fact that valves 2 are located on one side or on both sides of card 1, it is also possible that a second flexible film 7 is present on this other side. The upper 4 and lower 5 faces are connected together by an edge 6 which features a chamfered surface 19 on at least one of the sides, as is shown in FIGS. 1, 3 and 4 through 6.

The fluid or fluids in the test sample card 1 are displaced within this card 1 by means of a pressure or vacuum that is created. The movement of fluid in the direction of F6 in FIG. 6 is achieved by raising the pin 11 in the direction of F4, so that the flexible film can be distorted and the fluid can move in the direction of F5 as is clearly displayed.

Figure 7:
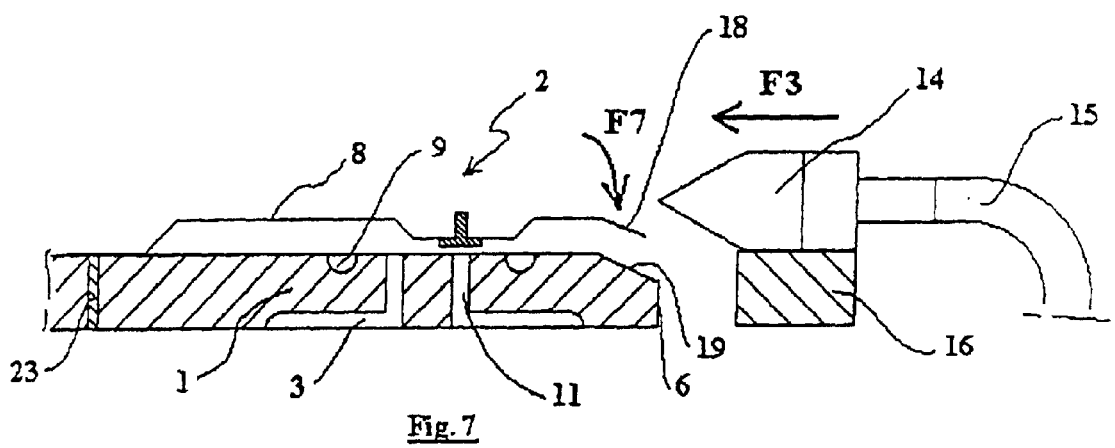
FIG. 7 represents a cross-sectional view identical to FIG. 3, although the tab has a different structure and operates in a manner opposite that of the previous figures.

According to a second embodiment of the invention, the role of said flexible tab 8 can be reversed. Thus, in FIG. 7, it can be seen that the flexible tab according to another embodiment features a closing means or wedge 18 at its free end which is opposite of that shown in other FIGS. 1 through 3. It can be noted that the piston-type actuator 14 does not act below the wedge 18 but on top of it, in such a manner that when said piston-type actuator 14 is in position, as shown in FIG. 7, the valve is open. However, as soon as compressed air is injected in the direction of F1, the actuator moves in the direction of F3 and the tab moves in the direction of F7, that is downward which closes the underlying valve.

A card 1 according to this invention thus has a more or less parallelepiped shape, preferably a rectangular parallelepiped. All of the edges 6 are thus linear and are thus capable of receiving valves 2 according to the invention, such as described above.

Preferably, at least one of the two long edges 6 only feature valves 2. In FIG. 13, only one edge 6 is partially represented as only four adjacent valves are represented.

FIG. 12 represents the three essential areas which form the device. There are, inserted into the device, the inspection area 32 on the left, and the storage area 31 of the cards 1 on the right, and an intermediate area 33 which serves as an interface between the storage area 31 and the inspection area 32.

The storage area 31 consists of a storage drawer for example, not shown, featuring grooves designed to position each card 1 with constant spacing between the cards 1.

The inspection area 32 consists of a framework featuring two uprights or worm screws 27, which, by turning simultaneously, allow the movement of a mobile trolley 16 which supports all of the piston-type actuators or electromagnet-type actuator 14. Each of these electromagnet-type actuators 14 has a piston which can be moved longitudinally from the left to the right of FIGS. 12 and 13 or vice versa.

The intermediate area 33 thus forms the link between areas 31 and 32 described above. The intermediate area 33 consists of the following:
 a fixed guide plate 25 for the valve 2 maneuvering pins 24, the valves 2 being supported by the cards 1 located in the storage area 31, as a result of the application of the electromagnet-type actuators 14 of the inspection area 32,
 a programming grid or mobile counter plate 26 which allows the pins 24 to be held in their given position, and said maneuvering pins 24.

In FIGS. 12 and 13, it can be seen that there are as many pins 24 as there are valves 2, although there is just one electromagnet-type actuator 14 for the valves 2 of the same card 1. Of course, this is not limiting and it is possible to have several electromagnet-type actuators 14 for the valves 2 of the same card 1.

Programming of the position of the valves, either open or closed, is thus performed by removing the counter plate 26 in order to disengage the previous positions of the pins 24, by activating the electromagnet-type actuators 14 in order to place said pins 24 in either an "in" or "out" position in relation to said plate 26, and by replacing the counter plate 26 so that the position of the pins is in relation with the open or closed valves that are desired. Tests have shown that only 100 milliseconds (ms) are required to program all of the valves 2 located in the same plane on the cards 1, by means of all the actuators 14. When there are ten (10) valves 2 per card 1 and ten (10) cards 1 are activated, 2.5 seconds are required to change the configuration of four hundred seventy (470) valves 1.

Each maneuvering pin 24 consists of an active part 29 and a shoulder 30 forming a stop, the assembly having a general "nail" shape. The active part 29 easily slides in the bore 34 provided in the plate 25, but also in the groove of the plate 26 designed to hold the shoulder 30 in position. However, said shoulder 30 is blocked between plate 25 and plate 26 when the pin 24 opens the valve 2, and is blocked only by plate 26 when said pin 24 closes said valve 2.

The plate 25 thus appears as a grid having as many bore holes 34 as there are pins 24. As for it, the plate 26 looks like a "comb".

If it is easy to understand the movement of the pins 24 from the retracted position to the extended position, with reference to FIGS. 12 and 13, as only the deployment of the electromagnet is all that is needed, things would be different for the opposite movement. Thus, in order to shift from the extended position to the retracted position, it is possible to magnetize the free end of the electromagnet which is in contact with said pin 24 or to insert a spring between the pin 24 and the counter plate 26 or any other means of prior art. It is also worth providing all means which allows said pins 24 to be held in the bores 34.

The presence of O-rings 28 should also be noted between said plates 25 at the level of the bores 34, as well as the maneuvering plate 24.

REFERENCES

1. Test sample card
2. Valve
3. Channel
4 and 5. Faces of the card 1
6. Edge of the card 1
7. Flexible film and/or which can be distorted
8. Compression means of the film 7 or flexible tab
9. Recession or groove peripheral to the valve 2
10. Peripheral weld located in the bottom of the groove 9
11. Hermetic closure means or elastomer pin
12. Opening device or wedge
13. Strip assembly consisting of several tabs 8
14. Piston or programming electromagnet type actuator
15. Compressed air hose
16. Mobile trolley or support
17. Compartment of the card 1
18. Bevel or closing means
19. Beveled surface of the card 1
20. Body of the card according to prior art
21. Film according to prior art
22. Weld between the body of the card 20 and the film 21
23. Strip assembly 13 securing means
24. Maneuvering pin
25. Fixed guide plate for pins 24
26. Mobile counter plate or programming grid
27. Worm screw
28. Ring seal
29. Active part of each pin 24
30. Shoulder forming a stop on each pin 24
31. Storage area
32. Inspection area
33. Intermediate area used as an interface between the storage area 31 and inspection area 32
34. Bore in the plate 25 designed to allow the pins 24 to slide
35. Grove in the plate 26 designed to hold the shoulder 30 in position
F1. Inlet of compressed air for actuating means 12
F2. Outlet of compressed air for actuating means 12
F3. Movement of actuating means 12
F4. Tipping of the tab 8
F5. Fluid transfer at the valve 2 level
F6. Fluid movements at the card 1 level
F7. Tipping of the tab according to the embodiment of FIG. 7

What is claimed is:

1. A valve, crossed by at least one channel, allowing to direct at least one fluid displaced by transfer means within a test sample card, the card featuring two faces connected to one another by an edge, wherein said valve comprises a flexible film, and/or which can be distorted, part of which is fixed to at least one of the faces of said card, and a film compression means, which may be activated or deactivated, and wherein a securing of the film on the card is made on at least one of the faces, by means of a securing feature located at the level of a recess provided around the valve.

2. The valve of claim 1, wherein the securing of the film on the card is peripheral to a set of channels associated with the valve, comprising at least one fluid entry channel and at least one fluid exit channel, whether the fluids are identical or different.

3. The valve of claim 1, wherein the securing is ensured by a heat seal peripheral to the valve.

4. The valve of claim 1, wherein the compression means acts on the film at the intersection point between at least one of the channels of the valve and one of the two faces of the card.

5. The valve of claim 1, wherein the compression means comprises a flexible tab.

6. The valve of claim 1, wherein the compression means features a closing means, and an opening and closing means, which synergizes with the actuation mechanisms.

7. The valve of claim 6, wherein said closing means comprises an elastomer pin.

8. The valve of claim 6, wherein said opening and closing means comprises a wedge.

9. The valve of claim 1, wherein the film on the valve is in contact with the plane face of the card, when said valve is in closed position, and is lifted in relation to said plane face, when the valve is in open position.

10. A test sample card comprising at least two valves of claim 1, which are positioned side by side and are fully or partly distributed along at least one edge of said card, and provided with compression means dedicated to the compression of the valves, positioned side by side.

11. The card of claim 10, having a substantially parallelepiped arrangement, wherein the edge(s) where the valves are located, is (are) rectilinear, and in that the distance separating said edge in relation to the location of each valve is constant.

12. The card of claim 10, wherein two adjacent valves positioned side by side are separated by a space between 1 and 5 mm.

13. The card of claim 12, wherein said space has a value selected from the group consisting of 3.96 mm, 2.54 mm and 1.28 mm.

14. A device for enabling the implementation of several cards, said cards being defined according to claim 10, said device comprising a storage area for the cards which are placed parallel to one another, with all of the valves on the same edge located within the same plane facing an intermediate area, a valve opening and closing inspection area associated with a manual or automatic control system, and made up of actuators, for which longitudinal movements take place in the direction of said intermediate area, and said intermediate area which serves as an interface between the storage area and the inspection area, this intermediate area comprising maneuvering pins having at least two positions, one position which allows opening and the other allowing closure of valves.

15. The device of claim 14, wherein the device has one actuator per card, and wherein there is one maneuvering pin per valve.

16. The device of claim 14, wherein the movement of the actuator is coaxial to the longitudinal axis of the maneuvering pin and the valve, which is activated or deactivated.

17. The device of claim 14, wherein the set of actuators are mounted in the same plane and are mobile along an axis parallel to the plane formed by all of the edges of the cards having the valves which can be activated by these actuators.

18. The device of claim 14, wherein the maneuvering pins have two possible positions, one allowing the opening and the other allowing the closure of the valves, each position being on each side of a confining element.

19. The device of claim 18, wherein the confining element is mobile between two extreme positions, one where it prevents the pins from moving, and the other where the movement of said pins is possible.

20. The device of claim 14, wherein said actuators comprises electromagnets.

21. The card of claim 10, wherein said compression means are connected together.

22. The valve of claim 1, wherein at least one of said faces is a plane face.

23. The valve of claim 1, wherein said recess is a groove.

* * * * *